US009649476B2

(12) United States Patent
Speck et al.

(10) Patent No.: US 9,649,476 B2
(45) Date of Patent: *May 16, 2017

(54) MEDICAL DEVICE FOR DISPERSING MEDICAMENTS

(71) Applicant: Bayer Intellectual Property Gmbh, Monheim (DE)

(72) Inventors: Ulrich Speck, Berlin (DE); Bruno Scheller, Saarbrucken (DE)

(73) Assignee: Bayer Intellectual Property GmbH, Monheim (DE)

( * ) Notice: Subject to any disclaimer, the term of this patent is extended or adjusted under 35 U.S.C. 154(b) by 758 days.

This patent is subject to a terminal disclaimer.

(21) Appl. No.: 13/866,547

(22) Filed: Apr. 19, 2013

(65) Prior Publication Data

US 2013/0231638 A1  Sep. 5, 2013

Related U.S. Application Data

(62) Division of application No. 12/782,989, filed on May 19, 2010, now Pat. No. 8,439,868, which is a division of application No. 10/528,577, filed as application No. PCT/DE03/02871 on Aug. 26, 2003, now Pat. No. 8,257,305.

(30) Foreign Application Priority Data

Sep. 20, 2002 (DE) .................. 102 44 847

(51) Int. Cl.
*A61M 25/10* (2013.01)
*A61L 29/08* (2006.01)
*A61L 29/16* (2006.01)
*A61L 31/16* (2006.01)
*A61L 31/08* (2006.01)
*A61M 25/00* (2006.01)

(52) U.S. Cl.
CPC ......... *A61M 25/1002* (2013.01); *A61L 29/08* (2013.01); *A61L 29/085* (2013.01); *A61L 29/16* (2013.01); *A61L 31/08* (2013.01); *A61L 31/16* (2013.01); *A61M 25/0045* (2013.01); *A61M 25/10* (2013.01); *A61M 25/1027* (2013.01); *A61L 2300/41* (2013.01); *A61L 2300/412* (2013.01); *A61L 2300/416* (2013.01); *A61L 2300/43* (2013.01); *A61M 25/104* (2013.01); *A61M 25/1038* (2013.01); *A61M 2025/0057* (2013.01); *A61M 2025/1004* (2013.01); *A61M 2025/105* (2013.01); *A61M 2025/1031* (2013.01); *A61M 2025/1075* (2013.01); *A61M 2025/1086* (2013.01)

(58) Field of Classification Search
CPC ......... A61M 25/1002; A61M 25/0045; A61M 25/10; A61M 25/1027; A61M 25/1038; A61M 25/104; A61M 2025/0057; A61M 2025/1004; A61M 2025/1031; A61M 2025/105; A61M 2025/1075; A61M 2025/1086; A61L 29/085; A61L 29/16; A61L 31/08; A61L 31/16; A61L 2300/41; A61L 2300/412; A61L 2300/416; A61L 2300/43

USPC ............ 604/96.01, 101.01, 103.02; 623/1.11
See application file for complete search history.

(56) References Cited

U.S. PATENT DOCUMENTS

| | | | |
|---|---|---|---|
| 4,101,984 | A | 7/1978 | MacGregor |
| 4,217,894 | A | 8/1980 | Franetzki |
| 4,247,352 | A | 1/1981 | Stupp |
| 4,305,926 | A | 12/1981 | Everse |
| 4,343,788 | A | 8/1982 | Mustacich |
| 4,364,921 | A | 12/1982 | Speck |
| 4,476,590 | A | 10/1984 | Scales |
| 4,479,795 | A | 10/1984 | Mustacich |
| 4,502,159 | A | 3/1985 | Woodroof |
| 4,532,315 | A | 7/1985 | Letoffe |
| 4,573,476 | A | 3/1986 | Ruiz |
| 4,677,143 | A | 6/1987 | Laurin |
| 4,769,013 | A | 9/1988 | Lorenz |
| 4,776,337 | A | 10/1988 | Palmaz |
| 4,793,825 | A | 12/1988 | Benjamin |
| 4,872,867 | A | 10/1989 | Joh |
| 4,879,135 | A | 11/1989 | Greco |
| 4,886,062 | A | 12/1989 | Wiktor |
| 4,909,799 | A | 3/1990 | Thulesius |
| 4,917,686 | A | 4/1990 | Bayston |
| 4,925,668 | A | 5/1990 | Khan |

(Continued)

FOREIGN PATENT DOCUMENTS

| | | |
|---|---|---|
| CA | 2 077539 | 7/1992 |
| CA | 2 132 936 | 3/1995 |

(Continued)

OTHER PUBLICATIONS

Adams, Johnathan D et al., "Taxol: a history of pharmaceutical development and current pharmaceutical concerns," Journal of the National Cancer Institute Monographs, 1993, pp. 141-147, No. 15.
Axel, Dorothea I. et al., "Paclitaxel Inhibits Arterial Smooth Muscle Cell Proliferation and Migration In Vitro and In Vivo Using Local Drug Delivery," Circulation, 1997, vol. 96, pp. 636-645.
Atkins, Peter, "Chapter 7: Simple Mixtures," Physical Chemistry, 6th ed., 1997, pp. 176-186.
Badapulle et al.: "A Hierarchical Bayesian Meta-Analysis of Randomised Clinical Trials of Drug-Eluting Stents", Lancet, 2004, vol. 364, pp. 583-591.
Barath et al., "Low Dose of Antitumor Agents Prevents Smooth Muscle Cell Proliferation After Endothelial Injury," JACC, 1989, vol. 13, No. 4, pp. 252A.

(Continued)

*Primary Examiner* — Manuel Mendez

(57) ABSTRACT

For selective treatment of diseased tissue sections or organ parts, the surface of medical devices entering into contact with areas thereof under pressure is coated with lipophilic substantially water-insoluble medicaments binding to various tissue components with good adherence thereto, said medicaments having an effect thereupon a short time after entering into contact therewith without exerting a harmful influence upon adjacent healthy tissue.

20 Claims, No Drawings

(56) References Cited

U.S. PATENT DOCUMENTS

| | | |
|---|---|---|
| 4,950,256 A | 8/1990 | Luther |
| 4,994,047 A | 2/1991 | Walker |
| 4,997,643 A | 3/1991 | Partain |
| 5,004,461 A | 4/1991 | Wilson |
| 5,019,096 A | 5/1991 | Fox |
| 5,019,393 A | 5/1991 | Ito |
| 5,019,601 A | 5/1991 | Allen |
| 5,051,257 A | 9/1991 | Pietronigro |
| 5,053,048 A | 10/1991 | Pinchuk |
| 5,059,166 A | 10/1991 | Fischell |
| 5,067,491 A | 11/1991 | Taylor |
| 5,098,977 A | 3/1992 | Fratuschi |
| 5,102,402 A | 4/1992 | Dror |
| 5,108,424 A | 4/1992 | Hoffman |
| 5,112,457 A | 5/1992 | Marchant |
| 5,135,516 A | 8/1992 | Sahatjian |
| 5,157,049 A | 10/1992 | Haugwitz |
| 5,163,952 A | 11/1992 | Froix |
| 5,165,952 A | 11/1992 | Solomon |
| 5,171,217 A | 12/1992 | March |
| 5,176,626 A | 1/1993 | Soehendra |
| 5,182,317 A | 1/1993 | Winters |
| 5,197,977 A | 3/1993 | Hoffman |
| 5,217,493 A | 6/1993 | Raad |
| 5,222,971 A | 6/1993 | Willard |
| 5,229,172 A | 7/1993 | Cahalan |
| 5,232,685 A | 8/1993 | Speck |
| 5,234,456 A | 8/1993 | Silvestrini |
| 5,244,654 A | 9/1993 | Narayanan |
| 5,282,823 A | 2/1994 | Schwartz |
| 5,288,711 A | 2/1994 | Mitchell |
| 5,298,255 A | 3/1994 | Sawamoto |
| 5,304,121 A | 4/1994 | Sahatjian |
| 5,306,286 A | 4/1994 | Stack |
| 5,314,688 A | 5/1994 | Kauffman |
| 5,320,634 A | 6/1994 | Vigil |
| 5,342,348 A | 8/1994 | Kaplan |
| 5,344,411 A | 9/1994 | Domb |
| 5,344,444 A | 9/1994 | Glastra |
| 5,345,933 A | 9/1994 | Peterson |
| 5,348,873 A | 9/1994 | Matsunda |
| 5,356,433 A | 10/1994 | Rowland |
| 5,370,614 A | 12/1994 | Amundson |
| 5,380,299 A | 1/1995 | Fearmot |
| 5,383,927 A | 1/1995 | De Golcoechea |
| 5,383,928 A | 1/1995 | Scott |
| 5,419,760 A | 5/1995 | Narciso |
| 5,443,458 A | 8/1995 | Eury |
| 5,447,724 A | 9/1995 | Helmus |
| 5,449,382 A | 9/1995 | Dayton |
| 5,454,886 A | 10/1995 | Burrell |
| 5,455,040 A | 10/1995 | Marchant |
| 5,456,663 A | 10/1995 | Lemelson |
| 5,457,113 A | 10/1995 | Cillinan |
| 5,464,450 A | 11/1995 | Buscemi |
| 5,464,650 A | 11/1995 | Berg |
| 5,500,013 A | 3/1996 | Buscemi |
| 5,504,102 A | 4/1996 | Agharkar |
| 5,510,330 A | 4/1996 | Martin |
| 5,531,716 A | 7/1996 | Luzio |
| 5,534,288 A | 7/1996 | Gruskin |
| 5,554,181 A | 9/1996 | Das |
| 5,554,182 A | 9/1996 | Dinh |
| 5,559,448 A | 9/1996 | Koenig |
| 5,567,495 A | 10/1996 | Modak |
| 5,569,463 A | 10/1996 | Helmus |
| 5,571,086 A | 11/1996 | Kaplan |
| 5,578,075 A | 11/1996 | Dayton |
| 5,605,696 A | 2/1997 | Eury |
| 5,607,463 A | 3/1997 | Schwartz |
| 5,607,475 A | 3/1997 | Cahalan |
| 5,609,629 A | 3/1997 | Fearmot |
| 5,624,411 A | 4/1997 | Tuch |
| 5,626,562 A | 5/1997 | Castro |
| 5,629,008 A | 5/1997 | Lee |
| 5,629,881 A | 5/1997 | Leeb |
| 5,643,580 A | 7/1997 | Subramaniam |
| 5,649,977 A | 7/1997 | Campbell |
| 5,674,192 A | 10/1997 | Sahatjian |
| 5,679,400 A | 10/1997 | Tuch |
| 5,681,846 A | 10/1997 | Trissel |
| 5,693,014 A | 12/1997 | Abele |
| 5,697,967 A | 12/1997 | Dinh |
| 5,716,981 A | 2/1998 | Hunter |
| 5,733,327 A | 3/1998 | Igaki |
| 5,762,638 A | 6/1998 | Shikani |
| 5,766,158 A | 6/1998 | Opolski |
| 5,770,198 A | 6/1998 | Coller |
| 5,772,640 A | 6/1998 | Modak |
| 5,789,018 A | 8/1998 | Engelson |
| 5,792,158 A | 8/1998 | Lary |
| 5,814,301 A | 9/1998 | Klopp |
| 5,820,607 A | 10/1998 | Tcholakian |
| 5,824,049 A | 10/1998 | Ragheb |
| 5,827,289 A | 10/1998 | Reiley |
| 5,837,008 A | 11/1998 | Berg |
| 5,863,745 A | 1/1999 | Fitzgerald |
| 5,873,904 A | 2/1999 | Ragheb |
| 5,886,026 A | 3/1999 | Hunter |
| 5,893,867 A | 4/1999 | Bagaisan |
| 5,902,283 A | 5/1999 | Darouiche |
| 5,916,596 A | 6/1999 | Desai |
| 5,921,952 A | 7/1999 | Desmond |
| 5,922,754 A | 7/1999 | Burchett |
| 5,954,706 A | 9/1999 | Sahatjian |
| 5,977,163 A | 11/1999 | Li |
| 5,980,972 A | 11/1999 | Ding |
| 5,981,568 A | 11/1999 | Kunz |
| 5,997,162 A | 12/1999 | English |
| 6,010,480 A | 1/2000 | Abele |
| 6,013,092 A | 1/2000 | Dehdashtian |
| 6,017,948 A | 1/2000 | Rubinfeld |
| 6,039,721 A | 3/2000 | Johnson |
| 6,071,285 A | 6/2000 | Lashinski |
| 6,096,070 A | 8/2000 | Raghab |
| 6,123,923 A | 9/2000 | Unger |
| 6,146,358 A | 11/2000 | Rowe |
| 6,171,232 B1 | 1/2001 | Papadreau |
| 6,177,061 B1 | 1/2001 | Klaveness |
| 6,203,487 B1 | 3/2001 | Consigny |
| 6,203,551 B1 | 3/2001 | Wu |
| 6,207,133 B1 | 3/2001 | Reszka |
| 6,214,333 B1 | 4/2001 | Zoldhelyi |
| 6,221,467 B1 | 4/2001 | Nazarova |
| 6,231,615 B1 | 5/2001 | Preissman |
| 6,240,616 B1 | 6/2001 | Yan |
| 6,248,100 B1 | 6/2001 | de Toledo |
| 6,258,108 B1 | 7/2001 | Lary |
| 6,264,624 B1 | 7/2001 | Desmond |
| 6,273,908 B1 | 8/2001 | Ndondo-Lay |
| 6,273,913 B1 | 8/2001 | Wright |
| 6,287,285 B1 | 9/2001 | Michal |
| 6,299,604 B1 | 10/2001 | Ragheb |
| 6,306,151 B1 | 10/2001 | Lary |
| 6,306,166 B1 | 10/2001 | Barry |
| 6,335,029 B1 | 1/2002 | Kamath |
| 6,339,039 B1 | 1/2002 | Porath |
| 6,355,058 B1 | 3/2002 | Pacetti |
| 6,364,856 B1 | 4/2002 | Ding |
| 6,369,039 B1 | 4/2002 | Palasis |
| 6,369,093 B1 | 4/2002 | Elbe |
| 6,375,931 B2 | 4/2002 | Ostensen |
| 6,400,448 B1 | 6/2002 | Sugawara |
| 6,406,754 B2 | 6/2002 | Chappa |
| 6,419,692 B1 | 7/2002 | Yang |
| 6,479,033 B1 | 11/2002 | Reszka |
| 6,491,619 B1 | 12/2002 | Trauthen |
| 6,491,938 B2 | 12/2002 | Kunz |
| 6,495,579 B1 | 12/2002 | Hunter |
| 6,500,341 B2 | 12/2002 | Wang |
| 6,503,954 B1 | 1/2003 | Bhat |
| 6,515,016 B2 | 2/2003 | Hunter |
| 6,544,223 B1 | 4/2003 | Kokish |
| 6,544,544 B2 | 4/2003 | Hunter |

(56) References Cited

U.S. PATENT DOCUMENTS

| | | |
|---|---|---|
| 6,562,024 B2 | 5/2003 | de Toledo |
| 6,575,888 B2 | 6/2003 | Zamora |
| 6,585,765 B1 | 7/2003 | Hossainy |
| 6,599,275 B1 | 7/2003 | Fischer |
| 6,599,448 B1 | 7/2003 | Ehrhard |
| 6,599,928 B2 | 7/2003 | Kunz |
| 6,616,591 B1 | 9/2003 | Toeh |
| 6,616,650 B1 | 9/2003 | Rowe |
| 6,635,082 B1 | 10/2003 | Hossainy |
| 6,638,913 B1 | 10/2003 | Speck |
| 6,656,156 B2 | 12/2003 | Yang |
| 6,682,545 B1 | 1/2004 | Kester |
| 6,682,546 B2 | 1/2004 | Amplatz |
| 6,695,811 B2 | 2/2004 | Samson |
| 6,706,892 B1 | 3/2004 | Ezrin |
| 6,730,064 B2 | 5/2004 | Ragheb |
| 6,774,278 B1 | 8/2004 | Ragheb |
| 6,867,190 B2 | 3/2005 | Carney |
| 6,918,927 B2 | 7/2005 | Bates |
| 7,060,051 B2 | 6/2006 | Palasis |
| 7,179,251 B2 | 2/2007 | Palasis |
| 7,419,683 B2 | 9/2008 | Szebeni |
| 7,445,792 B2 | 11/2008 | Toner |
| 7,491,234 B2 | 2/2009 | Palasis |
| 7,611,532 B2 | 11/2009 | Bates |
| 7,731,685 B2 | 6/2010 | Bates |
| 7,750,041 B2 | 7/2010 | Speck |
| 7,811,622 B2 | 10/2010 | Bates |
| 8,439,868 B2 * | 5/2013 | Speck .................. A61L 29/085 604/103.02 |
| 2001/0014717 A1 | 8/2001 | Hossainy |
| 2001/0034363 A1 | 10/2001 | Li |
| 2001/0037140 A1 | 11/2001 | Gaudoin |
| 2001/0044651 A1 | 11/2001 | Steinke |
| 2002/0013549 A1 | 1/2002 | Zhong |
| 2002/0032414 A1 | 3/2002 | Ragheb |
| 2002/0037358 A1 | 3/2002 | Barry |
| 2002/0098278 A1 | 7/2002 | Bates |
| 2002/0123505 A1 | 9/2002 | Burke |
| 2002/0193828 A1 | 12/2002 | Griffin |
| 2003/0007944 A1 | 1/2003 | O'Halloran |
| 2003/0028243 A1 | 2/2003 | Bates |
| 2003/0028244 A1 | 2/2003 | Bates |
| 2003/0036794 A1 | 2/2003 | Ragheb |
| 2003/0059454 A1 | 3/2003 | Barry |
| 2003/0100600 A1 | 5/2003 | Kinsella |
| 2003/0195548 A1 | 10/2003 | Kester |
| 2004/0068241 A1 | 4/2004 | Fischer |
| 2004/0073284 A1 | 4/2004 | Bates |
| 2004/0115228 A1 | 6/2004 | Costa |
| 2004/0224003 A1 | 11/2004 | Schultz |
| 2004/0243225 A1 | 12/2004 | Ragheb |
| 2005/0042295 A1 | 2/2005 | Hunter |
| 2005/0063926 A1 | 3/2005 | Bathina |
| 2005/0101522 A1 | 5/2005 | Speck |
| 2005/0123605 A1 | 6/2005 | Hunter |
| 2005/0222677 A1 | 10/2005 | Bates |
| 2005/0250672 A9 | 11/2005 | Speck |
| 2005/0278021 A1 | 12/2005 | Bates |
| 2006/0020243 A1 | 1/2006 | Speck |
| 2006/0020331 A1 | 1/2006 | Bates |
| 2007/0128118 A1 | 6/2007 | Yu |
| 2008/0010234 A1 | 1/2008 | Nakagawa |
| 2008/0012034 A1 | 1/2008 | Thielen |
| 2008/0102033 A1 | 5/2008 | Speck |
| 2008/0102034 A1 | 5/2008 | Speck |
| 2008/0118544 A1 | 5/2008 | Wang |
| 2008/0175887 A1 | 7/2008 | Wang |
| 2008/0255508 A1 | 10/2008 | Wang |
| 2008/0255509 A1 | 10/2008 | Wang |
| 2008/0255510 A1 | 10/2008 | Wang |

FOREIGN PATENT DOCUMENTS

| | | |
|---|---|---|
| CA | 2 207 025 | 6/1996 |
| CA | 2 218 103 | 10/1996 |
| CA | 2 345 729 | 4/2000 |
| CA | 2 345 697 | 5/2000 |
| CN | 1 224 622 | 8/1999 |
| DE | 42 25 553 | 5/1994 |
| DE | 43 34 272 | 4/1995 |
| DE | 43 41 478 | 6/1995 |
| DE | 44 35 652 | 4/1996 |
| DE | 44 46 694 | 6/1996 |
| DE | 195 14 104 | 11/1996 |
| DE | 69 119 753 | 1/1997 |
| DE | 69 403 966 | 2/1998 |
| DE | 197 24 796 | 12/1998 |
| DE | 101 15 740 | 10/2002 |
| DE | 10 244 847 | 4/2004 |
| DE | 69 925 936 | 7/2005 |
| DE | 201 22 736 | 7/2007 |
| EP | 1 118 325 | 11/1986 |
| EP | 0 357 003 | 3/1990 |
| EP | 0 470 246 | 2/1992 |
| EP | 0 551 182 | 7/1993 |
| EP | 0 578 998 | 1/1994 |
| EP | 0 604 022 | 6/1994 |
| EP | 0 623 354 | 11/1994 |
| EP | 0 673 114 | 9/1995 |
| EP | 0 681 475 | 11/1995 |
| EP | 0706376 | 4/1996 |
| EP | 0 717 041 | 6/1996 |
| EP | 0 747 069 | 12/1996 |
| EP | 0 797 988 | 10/1997 |
| EP | 0 829 238 | 3/1998 |
| EP | 0 975 340 | 2/2000 |
| EP | 1 407 786 | 4/2000 |
| EP | 1 037 605 | 9/2000 |
| EP | 1 090 637 | 4/2001 |
| EP | 1140273 | 10/2001 |
| EP | 1 159 974 | 12/2001 |
| EP | 1 250 166 | 10/2002 |
| EP | 1 447 098 | 8/2004 |
| EP | 1 512 398 | 3/2005 |
| EP | 1 521 603 | 4/2005 |
| EP | 1 536 850 | 6/2005 |
| EP | 1 666 070 | 6/2006 |
| EP | 1 666 071 | 6/2006 |
| EP | 1 669 091 | 6/2006 |
| EP | 1 669 092 | 6/2006 |
| EP | 1 372 737 | 8/2006 |
| EP | 1 695 697 | 8/2006 |
| EP | 1 695 698 | 8/2006 |
| EP | 1 735 042 | 12/2006 |
| EP | 1 781 209 | 5/2007 |
| EP | 2 092 941 | 8/2009 |
| EP | 2 092 942 | 8/2009 |
| EP | 2 098 230 | 9/2009 |
| JP | 06 063145 | 3/1994 |
| JP | 7500585 | 1/1995 |
| JP | 07 328124 | 12/1995 |
| JP | 10509691 | 9/1998 |
| JP | 11012160 | 1/1999 |
| JP | 2000 507930 | 6/2000 |
| JP | 2001-508320 | 6/2001 |
| JP | 2002-536058 | 10/2002 |
| JP | 3631777 | 3/2005 |
| PL | 212008 | 7/2012 |
| WO | WO 90/13293 | 11/1990 |
| WO | WO 90/13332 | 11/1990 |
| WO | WO 91/12779 | 9/1991 |
| WO | WO 92/11890 | 7/1992 |
| WO | WO 92/11896 | 7/1992 |
| WO | WO 92/12717 | 8/1992 |
| WO | WO 92/15282 | 9/1992 |
| WO | WO 92/20718 | 11/1992 |
| WO | WO 93/06792 | 4/1993 |
| WO | WO 93/07875 | 4/1993 |
| WO | WO 93/09762 | 5/1993 |
| WO | WO 93/09765 | 5/1993 |

(56) References Cited

FOREIGN PATENT DOCUMENTS

| | | |
|---|---|---|
| WO | WO 93/11120 | 6/1993 |
| WO | WO 93/11668 | 6/1993 |
| WO | WO 94/07484 | 4/1994 |
| WO | WO 94/07529 | 4/1994 |
| WO | WO 94/16706 | 8/1994 |
| WO | WO 94/23787 | 10/1994 |
| WO | WO 94/25020 | 11/1994 |
| WO | WO 94/26291 | 11/1994 |
| WO | WO 95/03036 | 2/1995 |
| WO | WO 95/03083 | 2/1995 |
| WO | WO 95/03795 | 2/1995 |
| WO | WO 95/15782 | 6/1995 |
| WO | WO 96/17629 | 6/1996 |
| WO | WO 96/20718 | 7/1996 |
| WO | WO 96/25176 | 8/1996 |
| WO | WO 96/25282 | 8/1996 |
| WO | WO 96/38183 | 12/1996 |
| WO | WO 96/39949 | 12/1996 |
| WO | WO 96/39970 | 12/1996 |
| WO | WO 97/01327 | 1/1997 |
| WO | WO 97/17098 | 5/1997 |
| WO | WO 97/26862 | 7/1997 |
| WO | WO 97/31674 | 9/1997 |
| WO | WO 97/33552 | 9/1997 |
| WO | WO 97/41916 | 11/1997 |
| WO | WO 98/11933 | 3/1998 |
| WO | WO 98/14174 | 4/1998 |
| WO | WO 98/15282 | 4/1998 |
| WO | WO 98/24427 | 6/1998 |
| WO | WO 98/25176 | 6/1998 |
| WO | WO 98/30249 | 7/1998 |
| WO | WO 98/31415 | 7/1998 |
| WO | WO 98/36784 | 8/1998 |
| WO | WO 98/43618 | 10/1998 |
| WO | WO 98/47540 | 10/1998 |
| WO | WO 99/09729 | 2/1999 |
| WO | WO 99/12577 | 3/1999 |
| WO | WO 99/13916 | 3/1999 |
| WO | WO 99/19004 | 4/1999 |
| WO | WO 99/08729 | 5/1999 |
| WO | WO 99/25336 | 5/1999 |
| WO | WO 99/30684 | 6/1999 |
| WO | WO 99/55396 | 11/1999 |
| WO | WO 99/59556 | 11/1999 |
| WO | WO 99/62510 | 12/1999 |
| WO | WO 00/00023 | 1/2000 |
| WO | WO 00/00238 | 1/2000 |
| WO | WO 00/06152 | 2/2000 |
| WO | WO 00/10552 | 3/2000 |
| WO | WO 00/21584 | 4/2000 |
| WO | WO 00/32238 | 6/2000 |
| WO | WO 00/32267 | 6/2000 |
| WO | WO 00/44414 | 8/2000 |
| WO | WO 00/45744 | 8/2000 |
| WO | WO 00/47197 | 8/2000 |
| WO | WO 00/50105 | 8/2000 |
| WO | WO 01/24866 | 4/2001 |
| WO | WO01/49268 | 7/2001 |
| WO | WO 01/49338 | 7/2001 |
| WO | WO 01/54748 | 8/2001 |
| WO | WO 01/76525 | 10/2001 |
| WO | WO 01/83016 | 11/2001 |
| WO | WO 02/066092 | 8/2002 |
| WO | WO 02/076509 | 10/2002 |
| WO | WO 03/022264 | 3/2003 |
| WO | WO 03/026718 | 4/2003 |
| WO | WO 03/041686 | 5/2003 |
| WO | WO 03/048166 | 6/2003 |
| WO | WO 2004/006976 | 1/2004 |
| WO | WO 2004/022124 | 3/2004 |
| WO | WO 2004/028582 | 4/2004 |
| WO | WO 2004/028610 | 4/2004 |
| WO | WO 2005/089855 | 9/2005 |
| WO | WO 2005/112570 | 12/2005 |
| WO | WO 2006/023104 | 3/2006 |
| WO | WO 2008/063576 | 5/2008 |
| WO | WO 2009/051614 | 4/2009 |
| WO | WO 2009/051615 | 4/2009 |
| WO | WO 2009/051616 | 4/2009 |
| WO | WO 2009/051618 | 4/2009 |

OTHER PUBLICATIONS

Bartoli et al., "In vitro and In vivo Antitumoral Activity of Free, and Encapsulated Taxol," J. Microencapulation, 1990, vol. 7, No. 2, pp. 191-197.

Baron et al., "In vitro Evaluation of c7E3-Fab (ReoPro™) Eluting Polymer-Coated Coronary Stents," Cardiovascular Research, Jun. 2000, vol. 46, pp. 585-594.

Baumbach et al.: Local Drug Delivery: Impact of Pressure, Substance Characteristics and Stenting on Drug Transfer Into the Arterial Wall, Catheterization and Cardiovascualr Interventions, vol. 47, pp. 102-106 (1999), Wiley-Liss, Inc. BC Lippold, "Retardarzneiformen" in E. Nurnberg, Hagers Handbuch der pharmazeutischen Praxis, vol. 2, Springer-Verlag Berlin Heidelberg New York, $5^{th}$ edition, 1991, pp. 832-840.

Brunner, H. et al., "Synthesis and in vitro testing of hematoporphyrin type ligands in platinum (II) complexes as potent cytostatic and phototoxic antitumor agents," Inorganica Chimica Acta, 1997, vol. 264, pp. 67-79.

Buaayu KK, "Balloon catheter for intravascular dosing," Patent Abstracts of Japan, Publication Date: Mar. 8, 1994; English Abstract of JP-06 063145.

Bult, H., "Restenosis: a challenge for pharmacology," TIPS, Jul. 2000, vol. 21, pp. 274-279.

Charles, Roger et al., "Ceramide-coated ballon catheters limit neointimal hyperplasia after stretch injury in carotid arteries," Circulation Research, Aug. 18, 2000, pp. 282-288.

Consigny, P. Macke et al., "Local Delivery of an antiproliferative drug with use of hydrogel-coated angioplasty balloons," J. Vasc. Interv. Radiol., 1994, vol. 5, pp. 553-560.

Coomber, B. L. et al., "In vitro endothelial wound repair: Interaction of cell migration and proliferation," Arteriosclerosis, Mar. 1990, vol. 10, No. 2, pp. 215-222.

Coomber and Gotlieb, Arteriosclerosis, 1990, vol. 10, No. 2, pp. 215-222.

Cox et al., "Effect of Local Delivery of Heparin and Methotrexate on Neointimal Proliferation in Stendted Porcine Coronary Arteries," Coronary Artery Disease, 1992, vol. 3, pp. 237-248.

Creel, Christopher J. et al., "Arterial Paclitaxel distribution and deposition," Circulation Research, Apr. 28, 2000, pp. 879-884.

Cremers et al., "V1742—Paclitaxel-beschictete PTCA-Katheter: Gibt es Unterschiede? Einfluss von PACCOCATH und DIOR Ballonkathetern auf die Neointimaporliferation an Schweinekoronarien," Clin. Res. Cardiol.,2008, 97, Suppl. 1:V1742.

Cremers, B et al., "Comparison of two different paclitaxel-coated balloon catheters in the porcine coronary restenosis model," Clin. Res. Cardiol., 2009, vol. 98, pp. 325-330.

Dichek, D. A. et al., "Seeding of Intravascular stents with genetically engineered endothelial cells," Circulation, 1989, vol. 80, No. 5, pp. 1347-1353.

Ding, A., et al., "Association of Mitogen-Activated Protein Kinases with Microtubules in Mouse Macrophages," J. Exp. Med., vol. 183, Apr. 1996, 1899-1904.

Dordunoo, S. K. et al., "Release of taxol from poly(ε-caprolactone) pastes: effect of water-soluble additives," Jounral of Controlled Release, 1997, vol. 44, pp. 87-94.

Drachmann et al., "Neoinitimal thickening after stent delivery of paclitaxel: Charge in composition and arrest of growth over six month," J. Am. Coll. Cardiol., 2000, vol. 36, pp. 2325-2332.

Department of Health and Human Services Notice of Intramural Research Project, Oct. 1, 1993-Sep. 30, 1994; "Molecular Strategies to Treat Restenosis," 4 pp.

Department of Health and Human Services Notice of Intramural Research Project, Oct. 1, 1994-Sep. 30, 1995, "Local Delivery of Therapeutic Agents for the Prevention of Restenosis," 6 pp.

(56) References Cited

OTHER PUBLICATIONS

English Translation of Elke M: Kontrastmittel in der radiologischen Diagnostik, pp. 113-119, 3$^{rd}$ Edition, Georg Thieme Verlag Stuttgart New York, 1992.

Elke M: Kontrastmittel in der radiologischen Diagnostik, pp. 113-119, 3$^{rd}$ edition, Georg Thieme Verlag Stuttgart New York, 1992.

Engelmann et al.: "Determination of N-Octanol/ Water Partition and Membrane Binding of Cationic Porphyrins", International Journal of Pharmaceutics, 2007, vol. 329, pp. 12-18.

Forth, W. et al. "Allegemeine und spezielle Pharmakologie und Toxikologie," 7 Auflage. Heidelberg: Spektrum Akademischer Verlag, 1996, Chapter, 1, 2, 3.

Garcia-Martinez et al., "Effects of Taxol on Endothelial of the Developing Semilunlar Heart Valves in the Chicken Embryo," Acta Anat, 1988, vol. 133, pp. 282-288.

Gershlick et al., "Inhibition of Restenosis with a Paclitaxel-Eluting, Polymer-Free Coronary Stent: The European evaluation of pacliTaxel Eluting Stent (ELUTES) Trail," Circulation, 2004, vol. 109, pp. 487-493.

Gold, Victor et al., "Amount of Substance Concentration," Compendium of Chemical Technology: International Union of Pure and Applied Chemistry Recommendations, 1987, p. 19.

Grossmann, S, "Neuartige Zubereitungen Hemmung der Neointimaproliferation in verengten Arterien," Dissertation zur Erlangung des akademischen Grades des Doktors der Naturwissenschaften (Dr. rer. nat.), Nov. 2006.

Hamm, C. W. et al., "Guideline: Diagnostic Heart Catheter Examination," Clin Res Cardiol, 2008, vol. 97, pp. 475-512.

English Translation of Hamm, C. W. et al., "Guideline: Diagnostic Heart Catheter Examination," Clin Res Cardiol, 2008, vol. 97, pp. 475-512.

Heldman, Alan W. et al., "Paclitaxel Stent Coating Inhibits Neointimal Hyperplasia at 4 Weeks in a Porcine Model of Coronary Restenosis," Circulation, May 8, 2001, pp. 2289-2295.

Henry et al.: "'POBA Plus': Will the Balloon Regain Its Luster?", Circulation: Journal of the American Heart Association, 2008, vol. 118, pp. 1309-1311.

Herdeg et al. "Paclitaxel: EIN Chemotherapeutikum Zur Restenoseprophylaxe? Experimentelle Untersuchungen In Vitro Und In Vivo", Interventionelle Kardiologie, vol. 89, No. 5 (2000), pp. 390-397.

Herdeg et al.: "Local Paclitaxel Delivery for the Prevention of Restenosis: Biological Effects and Efficacy In Vivo", Journal of the American College of Cardiology, 2000, vol. 35, No. 7, p. 1969-1976.

Hiatt, "Drug-Eluting Stents for the Prevention of Restenosis: In Quest for the Holy Grail," Catheterization and Cardiovascular Interventions, vol. 55, pp. 409-417, 2002.

Hou, D. et al., "Intrapericardial paclitaxel delivery inhibits neointimal proliferation and promotes arterial enlargement after porcine coronary overstretch," Circulation, 2000, vol. 102, pp. 1575-1581.

Indolfi et al., "Smooth Muscle Cell Proliferation Is Proportional to the Degree of Balloon Injury in a Rat Model of Angioplasty," Circulation, 1995, vol. 92, pp. 1230-1235.

Inoue, Teruo et al., "Comparison of Activation Process of Platelets and Neutrophils After Coronary Stent Implantation Versus Balloon Angioplasty for Stable Angina Pectoris," The American Journal of Cardiology, vol. 86, Nov. 15, 2000, pp. 1057-1062.

Jackson et al., "Current usage of contrast agents, anticoagulant and antiplatelet drugs in angiography and angioplasty in the UK," Clinical Radiology, 1995, pp. 699-704, vol. 50, No. 10.

Kalbitz et al., "Modulation der Wirkstoffpenetration in die Haut," Pharmazie, 1996, vol. 51, pp. 619-637.

Kandarpa et al., "Mural Delivery of Iloporst with Use of Hydrogel-coated Balloon Catheters Suppresses Local Platelet Aggregation," J. Vasc. Inter. Radiol., Nov./ Dec. 1997, vol. 8, pp. 997-1004.

Kandarpa et al., "Site-specific Delivery of Iloprost during Experimental Angioplasty Suppresses Smooth Muscle Cell Proliferation,"J. Vasc. Inter. Radiol., May/ Jun. 1998, vol. 9, pp. 487-493.

Karsch, Dr. "Lokale Applikation von Paclitaxel mit dem Schneider-Doppelballon," nach experimenteller Stentimplantation an den Koronaraterien des Schweines, Gießen 2001.

Kataoka, Toru et al., "7-Hexanoyltaxol-Eluting Stent for prevention of Neointimal Growth," Circulation, Oct. 1, 2002, pp. 1788-1793.

Katsuda et al., "The Role of Cytoplasmic Microtubules in Regulation of Smooth Muscle Proliferation," Clin. Ter. Cardiovasc.,1990, IX(4), pp. 245-248.

Khan, I. A. et al., "The Intra-vascular stent as a site-specific local drug delivery system," Drug Development and Industrial Pharmacy, 2005, vol. 31, pp. 59-78.

Kirk-Othmer, Encyclopedia of Chemical Technology, 3$^{rd}$ Edition, vol. 17, 1982, John Wiley & Sons, pp. 281-310.

Kolodgie, Frank D. et al., Local delivery of ceramide for restenosis: Is there a future for lipid therapy? Circulation Research, Aug. 18, 2000, pp. 264-267.

Kornowski, Ran et al., "Slow-Release Taxol Coated GRIT™ Stents Reduce Neointima Formation in a Porcine Coronary In-Stent Restenosis Model," 70th Scientific Sessions of the American Heart Association, Nov. 9-12, 1997.

Lamba, Nina M. K. et al., "Structure and Physical Characterization of Polyurethanes," Polyurethanes in Biomedical Applications ,Ch. 4, pp. 43-52, 1998, CRC Press.

Langer, R., "New methods of drug delivery," Science, Sep. 28, 1990, vol. 249, pp. 1527-1533.

Leo, Albert et al., "Partition Coefficients and Their Uses," Chemical Reviews, Dec. 1971, vol. 71, No. 6, pp. 525-616.

Licha et al.: "Hydrophilic Cyanine Dyes as Contrast Agents for Near-Infrared Tumor Imaging: Synthesis, Photophysical Properties and Spectroscopic In Vivo Characterization", Phtochemistry and Photobiology, 2000, vol. 72, No. 3, pp. 392-398.

Liggins, Richard T. et al., "Paclitaxel loaded poly(L-lactic acid) microspheres: properties of microspheres made with low molecular weight polymers," International Journal of Pharmaceutics, 2001, vol. 222, pp. 19-33.

Li et al: "Synthesis, Biodistribution and Imagain Properties of Indium-111-DTPA-Paclitaxel in Mice Bearing Mammary Tumors", Nucl. Med vol. 38 No. 7, 1042-47.

Lieu, C.-H., et al., "Role of Mitogen-Activated Protein Kinase in Taxol-Induced Apoptosis in Human Leukemic U937 Cells," Cell Growth & Differentiation, vol. 9, pp. 767-776, Sep. 1998.

Liggins, R. T. et al., "Solid-State Characterization of Paclitaxel,"J. Pharma. Sci., 1997, vol. 86, pp. 1458-1463.

Long et al.: "Perflucorocarbon Compounds as X-Ray Contrast Media in Lungs", Bulletin Societe Interanationale De Chirurgie, 1975, vol. 34 No. 2, pp. 137-141.

Lübbe, A. S. et al., "Preclinical experiences with magnetic drug targeting: Tolerance and Efficacy," Cancer Research, 1996, vol. 56, pp. 4694-4701.

Manderson et al., "Balloon Catheter Injury to Rabbit Cartoid Artery. I. Changes in smooth muscle phenotype," Artheriosklerosis, 1989, vol. 9, pp. 289-298.

Matthew, R. T. et al., "Synthesis and Evaluation of Some Water-Soluble Prodrugs and Derivatives of Taxol with Antitumor Activity," J. Med. Chem., 1992, vol. 35, pp. 141-151.

Mitchel et al., "Inhibition of Platelet Deposition and Lysis of Intrcoronary Thrombus during Balloon Angioplasty using Urokinase-Coated Hydrogel Balloons," Circulation, Oct. 1994, vol. 90, pp. 1979-1988.

Mortimer, C. et al., Basiswissen Chemie (excerpt) (1987).

Muller et al., "Colchicine and Antineoplastic Therapy for the Prevention of Restenosos after Percutaneous Coronary Interventions," JACC, 1990, vol. 17, No. 6, pp. 126B-131B.

Nairn, John A., "Polymer Characterization," Materials Science & Engineering 5473, 2003, Ch. 3, pp. 43-55.

Nicolaou, K. C. et al., "Design, synthesis and biological activity of protaxols", Nature, Jul. 29, 1993, vol. 364, pp. 464-466.

(56) References Cited

OTHER PUBLICATIONS

Nishio, K., et al., "Enhanced Interaction Between Tubulin and Microtubule-Associated Protein 2 Via Inhibition of Map Kinase and CDC2 Kinase by Paclitaxel," Int. J. Cancer: 63, 688-693 (1995).
Nuijen et al.: "Progress in the Development of Alternative Pharmaceutical Formulations of Taxanes", Investigational New Drugs, 2001, vol. 19, p. 143-153.
Oberhoff, Martin et al., "Local delivery of Paclitaxel using the double-ballon perfusion catheter before stenting in the porcine coronary artery," 2001,Catheterization and Cardiovascular Interventions, pp. 562-568, vol. 53.
Parker, Sybil P., "Micelle," McGraw-Hill Encyclopedia of Chemistry—Second Edition, 1992, pp. 638-639.
Phillips et al.: "A-Level Biology", Oxford University Press, 1989, p. 7-8.
Rowinsky, Eric K. et al., "Paclitaxel (Taxol)", Alastair JJ. Wood, ed. "Drug Therapy," The New England Journal of Medicine, vol. 332, No. 15, Apr. 13, 1995, pp. 1004-1014.
Sangster, J. et al., Octanol-Water Partition Coefficients: Fundamentals and Physical Chemistry, 1997, vol. 2 of Wiley Series in Solution Chemistry, pp. 1-49.
Scheller, Bruno et al., "Acute Cardiac Tolerance of Current Contrast Media and the New Taxane Protaxel Using Iopromide as Carrier During Porcine Coronary Angiography and Stenting," Investigative Radiology, vol. 37, No. 1, pp. 29-34.
Scheller et al. : "Pactlitaxel Balloon Coating, a Novel Method for Prevention and Therepy of Restenosis", Circulation: Journal of the American Heart Association, 2004, vol. 110, pp. 810-814.
Scheller et al.: "Addition of Paclitaxel to Contrast Media Prevents Restenosis After Coronary Stent Implanation", Journal of American College Radiology, 2003, vol. 42, pp. 1415-1420.
Scheller et al.: "Treatment of Coronary In-Stent Restenosis With a Paclitaxel-Coated Balloon Catheter", The New England Journal of Medicine, 2006, vol. 355, No. 20, pp. 2113-2124.
Schmitz, S. A. et al., "Superparamagnetic iron oxide-enhanced MRI of atherosclerotic plaques in Watanabe Hereditable Hyperlipidemic Rabbits," Investigative Radiology, Aug. 2000, vol. 35, No. 8, pp. 460-471.
Schwartz et al.: "Preclinical Restenosis Models and Drug-Eluting Stents", Journal of the American College of Cardiology, 2004 vol. 44, No. 7, pp. 1373-1385, Elsevier Inc.
Sharma, U. S. et al., "Pharmaceutical and Physical Properties of Paclitaxel (Taxol) Complexes with Cyclodextrins," J. Pharma. Sci., 1995, vol. 84, pp. 1223-1230.
Singla , AK et al.: "Paclitaxel and Its Formulations", International Journal of Pharmaceutics, 2002, vol. 235, pp. 179-192.
Signore, Pierre et al., "Complete Inhibition of Intimal Hyperplasia by Perivascular Delivery of Paclitaxel in Balloon-injured Rat Carotid Arteries," Laboratory Investigations, vol. 12, No. 1, Jan. 2001, pp. 79-88.
Slepian, from Textbook of Interventional Cardiology, 1990, Section IV, Chapter 32, pp. 647-670.
Sollott, Steven J. et al., "Taxol Inhibits Neointimal Smooth Muscle Cell accumulation after angioplasty in the rat," The Journal of clinical Investigation, Apr. 1995, vol. 95, pp. 1869-1876.
Speck et al. : "Inhibition of Restenosis in Stented Procine Coronary Arteries", Investigative Radiology, 2004, vol. 39, No. 3, pp. 182-186.
Speck, Ulrich—German Priority Document for file No. 101 15 740.1 filed on Mar. 26, 2001.
Swindell, C.S. et al., "Biologically Active Taxol Analogues with Deleted A-ring Side Chain Substituents and Variable C-2' Configurations," J. Med. Chem, 1991, vol. 34, pp. 1176-1184.
Tarr, B. D. et al., "A New Parenteral Vehicle for the Administration of Some Poorly Water Soluble Anti-Cancer Drugs," J. Parent Sci. Technol., 1987, vol. 41, pp. 31-33.
Tawashi, R. "The dissolution rates of crystalline drugs," J. Mond. Pharm. 1968, vol. 4, No. 11, pp. 371-379.

Tepe et al.: "Local Delivery of Paclitaxel to Inhibit Restenosis During Angioplasty of the Leg", The New England Journal of Medicine, 2008, vol. 358, No. 7, pp. 689-699.
Ulicky, L. et al., "Nernst's Distribution Law," Comprehensive Dictionary of Physical Chemistry, pp. 266-267, 1992.
Van Belle, E. et al., "Passivation of metallic stents after arterial gene transfer of phVEGF165 inhibits thrombus formation and intimal thickening," J. Am. Coll. Cardiol., 1997, vol. 29, pp. 1371-1379.
Voigt, R., Lehrbuch der pharmazeutishchen Technologie, 5th edition, VEB Verlag Volk und Gesundheit Berlin, 1984, p. 689.
Voisard et al., "The In-vitro Effect of Antineoplastic Agents on Proliferative Activity and Cytoskeletal Components of Plaque-Derived Smooth-Muscle Cells from Human Coronary Arteries," Coronary Artery Disease, 1993, vol. 4, pp. 935-942.
Werk et al.: "Inhibition of Restenosis in Femoropopliteal Arteries: Paclitaxel-Coated Versus Uncoated Balloon: Femoral Paclitaxel Randomized Pilot Trial", Circulation: Journal of the American Heart Association, 2008, vol. 118, pp. 1358-1365.
Wichert, B et al., "Low Molecular weight PLA: a suitable polymer for pulmonary administered microparticles?" J. Microencapsulation, 1993, vol. 10, No. 2, pp. 195-207.
Yushmanov, Victor E. et al., "Dipyridamole Interacts with the Polar Part of Cationic Reversed Micelles in Chloroform: 1H NMR and ESR Evidence," Journal of Colloid and Interface Science, 1997, vol. 191, pp. 384-390.
Clinical Cardiology Divergent Effects on Coronary Artery Disease: Abstract from 70th Scientific Session: Circulation, vol. 96, No. 8, Oct. 21, 1997.
Abstracts From the 70th Scientific Sessions, Circulation, Oct. 21, 1997, 96 Suppl. 1: 1-288.
English Abstract of CN 1 224 622, Aug. 4, 1999.
English Abstract of DE 19514104, Stemberger, Axel, Dr., "Coating for bio-material insertable into the bloodstream or tissue of the human body," Nov. 28, 1996.
English Abstract of DE 69925936, Stemberger, Axel, Dr., "High efficiency local drug delivery," May 11, 2006.
English Abstract of DE 4435652, Stemberger, Axel Dr., "Coating for bio-material to be used e.g. as sutures," Apr. 11, 1996.
English Abstract of EP 0 551 182, Morris, R. E. et al., "Method of treating hyperproliferative vascular disease using rapamycin, eventually in combination with mycophenolic acid," Jul. 14, 1993.
English Abstract of JP-06-063145, "Balloon Catheter for intravascular dosing," Buaayu KK, Patent Abstracts of Japan, Publication Date: Mar. 8, 1994.
English Abstract of JP-06-063145, "Balloon Catheter for Intravascular dosing," Buaayu KK, Thomson Innovation, Publication Date: Mar. 8, 1994.
English abstract of JP-07-500585, Thomson Innovation, Patent Record View, Publication Date: Jan. 19, 1995.
English Abstract of JP-07-328124, "Medicine dosing catheter," Terumo Corp., Patent Abstracts of Japan, Publication Date: Dec. 19, 1995.
English abstract of JP-10-509691, Thomson Innovation, Patent Record View, Publication Date: Sep. 22, 1998.
English Abstract of JP-11-012160, Jan. 19, 1999.
English Translation of Patent No. JP 3631777, Issue Date: Mar. 23, 2005. Publication No. 7-328124. Publication Date: Mar. 23, 2005. Application No. 06-122628. Filing Date: Jun. 3, 1994. Applicant: Terumo Corp. (Thomson Innovation).
Patent Family Listing for JP-2001 508320 (Publication Date: Jun. 26, 2001), Thomson Innovation.
Patent Family Listing for JP-2002 536058 (Publication Date: Oct. 29, 2002), Thomson Innovation.
English Abstract of WO 96/25282, Kaufmann, G. et al., "Process for producing a plastic cladding component and cladding component produced especially by said process," Aug. 22, 1996.
Thomson Innovation, Patent Record View, Publication Date: Jan. 19, 1995; English abstract of JP-7 500585.
Thomson Innovation, Patent Record View, Publication Date: Sep. 22, 1998; English abstract of JP-10 509691.
Herberts & Co Gmbh, "Liquid mixtures of photo-initiators, process for their production and their use," Espacenet, Publication Date: Nov. 26, 1992; English Abstract of WO-92 20718.

(56) References Cited

OTHER PUBLICATIONS

Strecker Ernst Peter Dr Med Pr., "Implantable percutaneous endoprosthesis," Espacenet, Publication Date: Jan. 19, 1994; English Abstract of EP-0 578 998.
"Water soluble paclitaxel prodrugs," Espacenet, Publication Date: Jun. 27, 2000; English Abstract of JP-2000 507930.
Magna International Toronto, "Process for producing a plastic cladding component and cladding component produced especially by said process," Espacenet, Publication Date: Aug. 22, 1996; English Abstract of WO-96 25282.
Terumo Corp., "Medicine dosing catheter," Patent Abstracts of Japan, Publication Date: Dec. 19, 1995; English Abstract of JP-07 328124.
Office Action issued Apr. 20, 2007 in U.S. Appl. No. 10/618,977, filed Jul. 14, 2003.
Office Action issued Oct. 13, 2011 in U.S. Appl. No. 11/763,116.
Office Action issued Aug. 16, 2011 in U.S. Appl. No. 12/835,420.
Office Action issued May 23, 2011 in U.S. Appl. No. 12/835,414.
U.S. Appl. No. 08/094,536 (Priority of D2).
U.S. Appl. No. 08/062,451 (Priority of D3).
English translation of Decision of Final Rejection, Japanese Application No. JP 2004-235694, issued Mar. 9, 2010.
Office Action issued Feb. 22, 2010 in U.S. Appl. No. 10/528,577.
Notice of Allowance issued Aug. 23, 2010 in U.S. Appl. No. 10/528,577.
Notice of Allowance issued Dec. 9, 2010 in U.S. Appl. No. 10/528,577.
Notice of Allowance issued Nov. 28, 2011 in U.S. Appl. No. 10/528,577.
File History of U.S. Appl. No. 60/395,434, filed Jul. 12, 2002.
File History of U.S. Appl. No. 60/244,446, filed Oct. 31, 2000.
Notice of Allowance issued Jun. 25, 2012 in U.S. Appl. No. 10/528,577.
Office Action issued Dec. 6, 2011 in U.S. Appl. No. 12/835,414.
Office Action issued May 9, 2012 in U.S. Appl. No. 12/835,414.
Office Action issued Mar. 9, 2012 in U.S. Appl. No. 12/835,420.
Notice of Allowance issued May 24, 2012 in U.S. Appl. No. 12/835,420.
Office Action issued Apr. 29, 2009 in U.S. Appl. No. 11/763,116.
Office Action issued Sep. 18, 2009 in U.S. Appl. No. 11/763,116.
Office Action issued Apr. 8, 2010 in U.S. Appl. No. 11/763,116.
Office Action issued May 7, 2012 in U.S. Appl. No. 11/763,116.
Final Rejection dated May 1, 2008 in related U.S. Appl. No. 10/528,577, filed Mar. 21, 2005.
Non-Final Rejection dated Jul. 2, 2007 in related U.S. Appl. No. 10/472,844, filed Sep. 26, 2003.
Final Rejection dated Nov. 1, 2007 in related U.S. Appl. No. 10/472,844, filed Sep. 26, 2003.
Non-Final Rejection dated May 29, 2008 in related U.S. Appl. No. 10/472,844, filed Sep. 26, 2003.
Final Rejection dated Mar. 4, 2009 in related U.S. Appl. No. 10/472,844, filed Sep. 26, 2003.
Non-Final Rejection dated Jan. 15, 2009 in related U.S. Appl. No. 10/618,977, filed Jul. 14, 2003.
Non-Final Rejection dated Apr. 20, 2007 in related U.S. Appl. No. 10/618,977, filed Jul. 14, 2003.
Judgment of Sep. 16, 2011 (Paper No. 52) from Interference No. 105,787.
Redeclaration of Interference (Paper No. 48) issued Sep. 13, 2011.
Applicants' Amendment of Sep. 12, 2011 (Paper No. 47), filed in U.S. Appl. No. 11/763,125, and cited in the Judgment of Sep. 16, 2011 in Interference No. 105,787.
International Preliminary Examination Report for PCT/DE2003/002871.
International Preliminary Examination Report for PCT/DE2001/04782.
International Search Report for EP 06 00 1041, Search Date: Apr. 11, 2006.
International Search Report for EP 06 00 1042, Search Date: Apr. 10, 2006.
International Search Report for EP 06 00 1040, Search Date: Apr. 11, 2006.
International Search Report for PCT/DE01/04782, Search Date: Dec. 27, 2002.
International Search Report for PCT/EP03/10480, Search Date: Feb. 20, 2004.
International Search Report for PCT/DE03/02871, Search Date: Feb. 17, 2004.
Elsevier Science Publishers, Amsterdam, NL; Jackson D.M. A. et al Current usage of contrast agents, anticoagulant and antiplatelet drugs in angiography and angioplasty in the UK. retrieved from STN Database accession No. 95327068 XP002226116.
"Balloon Catheter", en.wikipedia.org/wiki/balloon.catheter, 2008.
"Stent", www.thefreedictionary.com/stent, 2000.
"The Definition of Coated Stent", www.medterms.com, 2003.
Opposition of EP1,666,070.
Opposition of EP1,666,071.
Psychyrembel Klinishces Worterbuch, German Clinical Dictionary and Reference Book by Walter e Gruyter gmbH & Co. KG 1997, p. 717 (hyperplasia).
Online Extract From Sigma-Aldrich Web Site Concerning Poly Vinyl Alcohol (Molecular Weight: MW 500).
Online Extract From Sigma-Aldrich Web Site Concerning Poly Vinyl Alcohol (Molecular Weight: MS 1700).
Online Extract From MSDS Online Concerning Sucrose.
Online Extract From Polysciences, Inc. Web Site Concerning Poly Lactic Acid (Molecular Weight: MW 1600 to 2400).
Online Extract From Polysciences, Inc Web Site Concerning Polyvinylpyrrolidone (Molecular Weight: MW 2500).
Online Extract From Polysciences, Inc. Web Site Concerning Polycaprolactone (Molecular Weight: MW 2000).
Online Extract From Polysciences, Inc Web Site Concerning Polycaprolactone (Molecular Weight: MW: 1250).
Online Extract From Sigma-Alrich Web Site Concerning Poly Actylic Acid (Moleucalr Weight: MW 1800).
Extracts From the UK Trademarks Register (E7).
Print Out From an Online Tool for Calculating a Coefficient of Distribution Between Octanol and Water (E1A).
Heartwire, Jan. 22, 2003: Drugeluting Stents: Where Are They Now; p. 2, Communication of www.theheart.org.
Package Insert for Taxol.
Single e-mail from SIGMA Chemical Company of Feb. 15, 2007 to Dr. Sollot confirming that from 1991-1993 the material was listed in their catalog as "Taxol," and that the name was changed in their catalog from "taxol" to "paclitaxel" in 1994.
UK Court of Appeal Decision.
FDA Oncology Tools Approval Summary for Paclitaxel.
FDA Oncology Tools Product Label Details in Conventional Order for Paclitaxel.
Technical Leaflet Cremphor EL.
Untersuchungen in vitro and in vivo, Zeitschrift fur kardiologie, Band 89, Heft 5, 2000, pp. 390-397.
Printout from the website of Bayer HealthCare Pharmaceuticals, indicating that Ultravist has been commercially available since 1985.
Report demonstrating in the C6-ceramide is a lipophilic substance as defined by the patent in suit.
Office Action issued by the European Patent Office on Sep. 15, 2005.
Claims enclosed with Office Action issued by European Patent Office on Sep. 15, 2005.
Response filed on Jan. 13, 2006.
Product Information on the DIOR balloon catheter from Eurocor GmbH.
The decision to revoke EP1140273 B1 (=D11EP) of Oct. 23, 2007.
Clinical Cardiology Divergent Effects on Coronary Artery Disease: Abstract from 70th Scientific Session: Circulation, vol. 96, No. 8, Oct. 21, 2007.
Definition of "partition coefficient" Wikipedia.
Notice of Opposition to a European Patent. Patent No. 1 539 266 B1filed by Fish & Richardson on behalf of Boston Scientific Limited. Received in the EPO on Jul. 29, 2008 (49 pages).

(56) References Cited

OTHER PUBLICATIONS

Notice of Opposition. Objection to European Patent EU Patent 1 539 266 B1 filed by Karin Lindner-Vogt, European Patent Attorney on behalf of Opponent Biotronik VI Patent AG. English language (40 pages) and German languages (40 pages). Received in the EPO on Dec. 12, 2008. (Total pages 80).
Evidence and Arguments in support of the grounds for opposition. Filed by Jacobacci & Partner on behalf of Opponent INVATEC S.p.A. Proprietor: Bayer Schering Pharma Aktiengesellschaft. In re: Opposition against EP-B-1 539 266. Received in the EPO on Jan. 19, 2009. (7 pages).
Notice and Statement of Grounds of Opposition against EP 1 539 266 filed by Williams Powell on behalf of Opponent Cook Incorporated. Date: Jan. 8, 2009. (33 pages).
Opposition against EP 1 539 266 filed by Hoffmann-Eitle on behalf of Peter Klusman Jan. 9, 2009. (7 pages).
Formal objection against EP Patent EP 1 539 266 B1 filed by ABK Patent, Trademark and Designs Attorneys on behalf of Eurocor GmbH. Date: Jan. 6, 2009. In the German language. (45 pages).
Formal objection against EP Patent EP 1 539 266 B1 filed by ABK Patent, Trademark and Designs Attorneys on behalf of Eurocor GmbH. Date: Jan. 6, 2009. In the English language. (45 pages).
Reply to the Notices by Bayer Schering Pharma AG. Main Request and as Auxiliary Request I through IV. In the English language. Date: Nov. 23, 2009. (18 pages).
Reply by Bayer Schering Pharma AG. Main Request, Auxiliary Request II, III and IV. In the English language. Date: Nov. 23, 2009. (22 pages).
Reply to the Notices filed by Weickmann & Weickmann on behalf of the Proprietor Bayer Schering Pharma AG. Date: Nov. 23, 2009. In the German language. (37 pages).
Documents submitted in view of the new Auxiliary Requests filed by Fish & Richardson on behalf of Boston Scientific Limited. Date: Mar. 10, 2010. (33 pages).
Summons to oral proceedings in compliance with Rule 115(1) European Patent Convention EPC issued by the EPO with comments to help parties to systematically prepare for the proceedings. Dated Sep. 1, 2010. Application No. /Patent No. 03750300.0-1521/1539266. In the languages of English and German. (46 pages).
A pleading for the oral hearing on Feb. 16, 2011 submitted to the EPO filed by ABK Patent, Trademark and Designs Attorneys on behalf of Eurocor GmbH. Dated: Jan. 6, 2011. Re: New Documents Filed. In the language of English. (4 pages).
A pleading for the oral hearing on Feb. 16, 2011 submitted to the EPO by ABK Patent, Trademark and Designs Attorneys on behalf of Eurocor GmbH. Dated: Jan. 6, 2011. Re: New Documents Filed. In the language of German. EP Patent No. 1539266 B1. (4 pages).
Admissibility of the claims of the patent owner submitted to the EPO by ABK Patent, Trademark and Designs Attorneys on behalf of Eurocor GmbH. Dated: Jan. 4, 2011. EP Patent No: 1539266 B1. In language of English. (12 pages).
Admissibility of the claims of the patent owner submitted to the EPO by ABK Patent, Trademark and Designs Attorneys on behalf of Eurocor GmbH. Dated: Jan. 4, 2011. EP Patent No. 1539266 B1. In the language of German. (12 pages).
A pleading for the oral hearing on Feb. 16, 2011 submitted to the EPO according to Rule 115 (1) EPC by ABK Patent, Trademark and Designs Attorney on behalf of Eurocor GmbH. Dated: Jan. 4, 2011. In the language of English. EP Patent No. 1539266 B1. (4 pages).
A pleading for the oral hearing on Feb. 16, 2011 submitted to the EPO according to Rule 115 (1) EPC by ABK Patent, Trademark and Designs Attorney on behalf of Eurocor GmbH. Dated: Jan. 4, 2011. In the language of German. EP Patent No. 1539266 B1. (4 pages).
A submission for the oral hearing on Feb. 16, 2011 provided to the EPO according to Rule 115 (1) EPC by ABK Patent, Trademark and Designs Attorney on behalf of Eurocor GmbH. Dated: Jan. 4, 2011. In the language of English. EP Patent No. 1539266 B1. (20 pages).
A submission for the oral hearing on Feb. 16, 2011 provided to the EPO according to Rule 115 (1) EPC by ABK Patent, Trademark and Designs Attorney on behalf of Eurocor GmbH. Dated: Jan. 4, 2011. In the language of German. EP Patent No. 1539266 B1. (20 pages).
A further pleading for the oral hearing on Feb. 16, 2011 submitted to the EPO by ABK Patent, Trademark and Designs Attorney on behalf of Eurocor GmbH. Dated: Jan. 4, 2011. In the language of English. EP Patent No. 1539266 B1. (4 pages).
A further pleading for the oral hearing on Feb. 16, 2011 submitted to the EPO by ABK Patent, Trademark and Designs Attorney on behalf of Eurocor GmbH. Dated: Jan. 4, 2011. In the language of German. EP Patent No. 1539266 B1. (4 pages).
Newly submitted documents. Data Supplement to the scientific publication D4'n submitted to the EPO by ABK Patent, Trademark and Designs Attorney on behalf of Eurocor GmbH. Dated: Jan. 6, 2011. In the language of English. EP Patent No. 1539266 B1. (8 pages).
Newly submitted documents. Data Supplement to the scientific publication D4'n submitted to the EPO by ABK Patent, Trademark and Designs Attorney on behalf of Eurocor GmbH. Dated: Jan. 6, 2011. In the language of German. EP Patent No. 1539266 B1. (8 pages).
Correspondence dated Jan. 7, 2011. Submitted to the EPO by ABK Patent, Trademark and Designs Attorney on behalf of Eurocor GmbH. Re: Updated list of documents cited in the proceedings. In the languages of English and German. EP Patent No. 1539266 B1. (2 pages).
Further submissions for the hearing before the Opposition Division of the EPO. Re: Submitted documents. Submitted to the EPO by ABK Patent, Trademark and Designs Attorney on behalf of Eurocor GmbH. Re: Updated list of documents cited in the proceedings. In the languages of English and German. EP Patent No. 1539266 B1. Dated Jan. 12, 2011. (10 pages).
Submission by Bayer Schering Pharma. Claims modified in compliance with the main request and the auxiliary request I-IX supplied on the ruling dated Oct. 5, 2010. Exhibits, Main Request and auxiliary request I-IX. (pp. 78)
Submission by Bayer Schering Pharma. Claims modified in compliance with the main request and the auxiliary request I-IX supplied on the ruling dated Oct. 5, 2010. (38 pages).
A further submission for the hearing before the Opposition Division of the EPO on Feb. 14, 2011. Submitted to the EPO on Jan. 14, 2011 by ABK Patent, Trademark and Designs Attorney on behalf of Eurocor GmbH. Re: Updated list of documents cited in the proceedings. In the language of English. EP Patent No. 1539266 B1. (16 pages).
A further submission for the hearing before the Opposition Division of the EPO on Feb. 14, 2011. Submitted to the EPO on Jan. 14, 2011 by ABK Patent, Trademark and Designs Attorney on behalf of Eurocor GmbH. Re: Updated list of documents cited in the proceedings. In the language of German. EP Patent No. 1539266 B1. (6 pages).
Submission to the EPO by August & Debouzy Avocats on behalf of Invatek S.p.a. Dated Jan. 14, 2011. (2 pages).
Submissions in preparation for oral proceedings of Feb. 16, 2011. Submitted to the EPO by Williams Powell on behalf of Opponent IV Cook Inc. Dated: Jan. 14, 2011. (5 pages).
Submissions in preparation for oral proceedings of Feb. 16, 2011. Submitted to the EPO by Williams Powell on behalf of Opponent IV Cook Inc. Dated: Jan. 31, 2011. (6 pages).
Communication from the Examining Division of the European Patent Office issued on Sep. 15, 2005 in EP Application No. 03 750 300.0-1219. EP Patent No. 1539266.
Annex to the Communication from the Examining Division of the European Patent Office issued on Sep. 15, 2005 in EP Application No. 03 750 300.0-1219. EP Patent No. 1539266.
Reply and claims filed Jan. 13, 2006 in response to the Communication from the European Patent Office dated Sep. 15, 2005 in EP Application No. 03 750 300.0-1219. EP Patent No. 1539266.
Japanese Final Rejection in Co-pending Application No. JP2004-538694 dated Mar. 1, 2010. Mail date Mar. 9, 2010.
Opposition to corresponding EP1539266 by Boston Scientific Ltd., Mar. 10, 2010.
Series of extracts from the UK Trademarks Register, Apr. 29, 2008.

(56) References Cited

OTHER PUBLICATIONS

Press release of Jan. 17, 2007 regarding patent infringement suit (D49C).
Presentation Dr. Cortese, Jul. 9, 2010.
Abstracts From the 70$^{th}$ Scientific Sessions, Circulation, Oct. 21, 1997, 96 Suppl. 1 1-288.
Versuchsbeschreibungen (D44) ("Description of experiments"), Jul. 9, 2010.
Affidavit (D46), Jul. 9, 2010.
Final Report Study ACL435-43 (D47), May 14, 2009.
Summary Data Biotronik SE & Co. KG (D48), Jul. 9, 2010.
Submission BpatG (Ceramide Balloon Catheter) MLA HLA (D49), Jul. 9, 2010.
German Translation of Gericht zu's Gravenhage, 245392/HA ZA May 2016 (D49A).
IUPAC, Compendium of Chemical Terminology (1987).
Table of General Chemical Information, Oct. 12, 2009.
Product information DIOR balloon catheter of Eurocor GmbH, Oct. 1, 2008.
Declaration of Professor Dr. Schols, Oct. 1, 2008.
English Abstract of JP-06 063145, "Balloon Catheter for intravascular dosing," Buaayu KK, Patent Abstracts of Japan, Publication Date: Mar. 8, 1994.
English Abstract of JP-6 063145, "Balloon Catheter for Intravascular dosing," Buaayu KK, Thomson Innovation, Publication Date: Mar. 8, 1994.
English Abstract of JP-07 328124, "Medicine dosing catheter," Terumo Corp., Patent Abstracts of Japan, Publication Date: Dec. 19, 1995.
English translation of Decision of Final Rejection, Japanese Application No. 2004 235694, issued Mar. 9, 2010.
English Translation of JP 36371777 (Publication Date: Mar. 23, 2005), Thomson Innovation.
Submission by Eurocor, filed Feb. 18, 2011, in EPO Opposition against EP 1 539 266.
English Translation of Submission by Eurocor, Feb. 18, 2011, in EPO Opposition against EP 1 539 266.
Minutes of Oral Hearing, May 3, 2011, in Opposition against EP 1 539 266.
English translation of Minutes of Oral Hearing, May 3, 2011, in Opposition against EP 1 539 266, issued May 3, 2011.
EPO Decision to revoke EP 1 539 266, in EPO Opposition against EP 1 539 266.
English Translation of Decision to revoke the EP Patent, in EPO Opposition against EP 1 539 266.
Grounds of Appeal, filed Sep. 12, 2011, by Bayer Pharma AG, in EPO Opposition against EP 1 539 266 (with Main and Auxiliary Requests).
English Translation of Grounds of Appeal, filed Sep. 12, 2011, by Bayer Pharma AG, in EPO Opposition against EP 1 539 266 (with Main and Auxiliary Requests).
Response to Appeal, filed Oct. 13, 2011 by Boston Scientific, in EPO Opposition against EP 1 539 266.
Response to Appeal, filed Jan. 20, 2012 by Cook Inc., in EPO Opposition against EP 1 539 266.
Response to Appeal, filed Jan. 26, 2012 by Dr. Peter Klusmann, in EPO Opposition against EP 1 539 266.
Cancellation Action against DE 203 21 606 filed in the German Patent Office by Eurocor (Sep. 6, 2010).
English Translation of Cancellation Action against DE 203 21 606 filed in the German Patent Office by Eurocor (Sep. 6, 2010).
Submission by Bayer Schering Pharma (BSP) filed Feb. 25, 2011 in Cancellation Action against DE 203 21 606.
English Translation of Submission by Bayer Schering Pharma (BSP) filed Feb. 25, 2011 in Cancellation Action against DE 203 21 606.
Submission by Eurocor filed Apr. 20, 2011 in Cancellation Action against DE 203 21 606.
English Translation of Submission by Eurocor filed Apr. 20, 2011 in Cancellation Action against DE 203 21 606.
Submission by Bayer Schering Pharma (BSP) filed Sep. 30, 2011 in Cancellation Action against DE 203 21 606.
English Translation of Submission by Bayer Schering Pharma (BSP) filed Sep. 30, 2011 in Cancellation Action against DE 203 21 606.
Submission by Eurocor filed Dec. 2, 2011 in Cancellation Action against DE 203 21 606.
English Translation of Submission by Eurocor filed Dec. 2, 2011 in Cancellation Action against DE 203 21 606.
Office Action issued Dec. 16, 2011 in U.S. Appl. No. 12/835,414.
Office Action issued Feb. 16, 2012 in U.S. Appl. No. 12/782,989.
English Translation of DE 4225553 (2011).
Charles, R. et al. Data Supplemental, Circulation Research, 87:282 (2000).
International Program on Chemical Safety, General Chemical Information Chart. (www.inchem.org).

* cited by examiner

MEDICAL DEVICE FOR DISPERSING MEDICAMENTS

This invention relates to a medical apparatus that releases drugs for the selective therapy of specific tissues or organ parts and to a method of manufacturing such drug-coated devices.

Numerous diseases do not affect the entire organism at the same time but are restricted to specific tissues, often even to very limited individual tissue areas or organ parts. Examples can he found among tumor, joint and vascular diseases.

Pharmacotherapy of such diseases generally is effected by oral or intravenous administration of drugs that spread throughout the body and cause undesirable side effects in healthy tissues and organs, especially when the disease to be treated is in a severe stage, which limit the therapeutic application. The diseased tissues could be treated either selectively using drugs that specifically bind to diseased tissue (e.g. antibodies) while the administration path is maintained, or by selective administration, e.g. direct injection into the diseased tissue or supply via a catheter to the blood vessels that feed the diseased tissue. In case of selective administration may problems arise due to the short period of time during which the drugs are efficacious and the invasive administration paths, as repeated administration is not an option. When drugs are selectively administered via the bloodstream that feeds the diseased tissue, there is the additional problem that the drugs are insufficiently extracted when the blood or active agent solution swiftly flows through the blood vessels.

These problems used to be addressed by various pharmaceutical preparations with sustained release of the active agent, drug-releasing implants or selective access paths that stay operational for a longer period of time such as implanted catheters, etc.

It is known that the surface of medical equipment inserted into the body, in particular, of catheters, can be coated with agents that enhance gliding quality or prevent blood coagulation but have no therapeutic effect.

In addition, catheters are equipped with special devices for injecting drugs into the arterial wall, for example, using needles or a perforation of the catheter wall that sits adjacent to the vessel wall and through which the drug is injected at high pressure.

Other principles are based on extending the contact time between the arterial wall and an active agent preparation administered via the catheter by either blocking the blood flow for a sufficient period of time, e. g. using dual balloon catheters in which the active agent solution is contained in a chamber between the balloons, or by voids between a toric outer wall of the balloon allowing a limited flow of blood through a canal that passes through the balloon.

According to U.S. Pat. No. 5,102,402, drugs in the form of microcapsules are inserted into preformed recesses of balloon catheters for delayed release of the active agent. When the balloon is inflated, the microcapsules are to be pressed against the vessel wall, remain there and slowly release the active agent(s). Many authors propose to apply drugs embedded in hydrogel onto balloon catheters while they do not specify the function of the hydrogel, i. e. to act as an adhesive, to improve the gliding quality, or for controlled drug release.

A disadvantage of the products mentioned above is their complex structure, which causes production, quality control, and cost problems and forces additional aggravating working steps on doctors and patients when applied. Some of the methods mentioned may result in undesirable vascular damage in excess of the intended dilatation of the vessel. Another setback is that each measure aimed at extending contact time entails another reduction in blood and oxygen supply to the downstream tissues.

For the sake of completeness, we also refer to a device for preventing restenosis as described in WO 01/24866 that is coated with a lipid ceramide substance derived from natural cell membranes. This substance is used because of its affinity to cell walls that is not found in common drugs. Experts in the field continue to state that restenosis prevention using drugs requires release of the active agent over a period of several days.

The problem underlying the present invention is to provide a device for the release of drugs into specific tissue areas or organ parts that has a strong therapeutic effect without damaging healthy tissue, which is sufficiently well tolerated, and can be produced and applied with a minimal effort.

This problem is solved according to the invention by a device designed or produced in accordance with the characteristics of claims 1 and 15. The subordinate claims disclose further characteristics and advantageous improvements of the invention.

The invention provides improved drug-carrying balloon catheters or similar medical devices manufactured in a simple process that are highly versatile and facilitate the immediate release of active agents. Surprisingly, and contrary to the currently acknowledged opinion, no continuing release of the active agent from an inert matrix (polymer, hydrogel, microcapsule, etc.) and no special chemical or physical state of the active ingredients is required or useful. Therefore, no sophisticated techniques for producing or controlling depot formulations are required.

Coating balloons on catheters with drugs according to this invention is particularly useful because there is a frequent need for treatment after blood vessels or other passages in the body were dilated with balloons to prevent stenosis or an occlusion of the lumen created by the pressure of the balloon, to limit tumor growth or to enhance healing processes including the formation of collateral circulation. This can be achieved by drugs that become effective in the immediate vicinity of the balloon surface. The drugs firmly adhere to the balloon while passing through arteries with an intense blood flow on their way to their target until the balloon is inflated, and an effective dose is released in the short time (sometimes just a few seconds) during which the inflated balloon is in contact with the tissue, absorbed by the tissue in such a way that the blood flow that resumes immediately after the balloon is deflated does not rinse it off.

The subjects for coating are wires of the invention used to guide catheters, needles and catheters or catheter parts that are pressed against the diseased tissue at least for a short time. Preferred catheter materials are polyamides, polyamide mixtures and copolymers, polyethylene terephthalate, polyethylene and copolymers, polyurethane, natural rubber and its derivatives. The lengths and diameters of the catheter or balloon areas designated for pharmacological treatment are not of any decisive importance for their application as the dosage is calculated in μg of active agent/$mm^2$ of surface area. For example, balloons with diameters ranging from 2 to 4 mm and lengths ranging from 1.0 to 4.0 cm are commonly used for coronary dilatation. Balloons up to >20 mm in diameter and up to >10 cm in length can be used for other vessels. The surfaces to be coated may be smooth (i.e. without a special structure for absorbing the active agents), roughed up or comprise any structure; while no special surface structures are required for the active agents to adhere, such structures also do not impede adhesion. Adhesion of the active agents to the balloon surfaces is exclusively caused by selecting suitable solvents and, optionally, adding substances that influence adhesion. It is even surprisingly strong on completely smooth balloon surfaces.

All surfaces can additionally be coated with substances that improve the gliding quality of the products, prevent blood from coagulating on the surface or improve any other properties of these medical products have but the materials used for coating do not have to be released into the environment and this additional coating does not noticeably reduce the release of the active agents for treatment of the target tissue and thus the product's efficacy.

Balloon catheters are formed by dilating a segment of 1 cm to ca. 10 cm length of very thin plastic tubes. The dilated, very thin-walled balloon membrane is then folded several times along the catheter axis and wrapped tightly around the catheter axis so that the dilated area, when folded, is only slightly greater in diameter than the rest of the catheter. The tight folding of the balloon membrane is required for passing the balloon catheter through access ports, guiding catheters and heavily stenosed sections of blood vessels.

The balloons of catheters can be coated when folded or when unfolded. The process always provides an intact and sufficiently uniform surface coating, and the active agents adhere to the surface of the balloon catheter even when it is refolded after being coated when unfolded.

A balloon that was coated when unfolded is produced without any impact on the coating, for example by using balloon membranes with preformed folds and bends whose structure is not lost due to dilatation and which allow the balloon membrane to refold at least loosely when the pressure is discharged from the balloon without requiring an external force as primary cause. It is only after this prefolding that the preformed folds are compressed by external pressure or by a vacuum. Folds are in no way required to hold the active agent. In addition refolding can be achieved using minor mechanical force by very smooth materials, and the tools used may also be wetted by slippery biocompatible liquids in which the active ingredients do not or, at least, do not well dissolve.

In accordance with another variant of the invention, the balloons of readily folded balloon catheters are coated by dipping them into low-viscosity active agent solutions. Solvent and active agent penetrate into the extremely dense folds where they form a surprisingly uniform coat that contains a reproducible dose and is not damaged by any subsequent step. The solution or, after the solvent has dried, the coat that adheres to the outer surface may be left there or may be removed in another step so that only the active agent portion that sits inside the folds of the balloon is retained.

After coating, when the balloon is folded, a stent can be pulled over the balloon catheter and firmly pressed onto it. The only step still required is sterilization, e. g. using ethylene oxide.

The work cycle laid out like this is extremely simple, hardly susceptible to failures, and can be carried out even with mechanically, chemically and physically sensitive coating materials. It was found that coating using this method does not result in any undesirable loosening or sticking together of the folds and that the active agent applied in this way adheres firmly enough to not be rinsed off by the bloodstream but releases most of the active agent when the balloon is inflated in the target tissue.

Suitable drugs are lipophilic, mostly water-insoluble and strongly acting drugs that bind to any tissue components. Drugs are called lipophilic when their butanol to aqueous buffer solution (pH 7) distribution ratio is 0.5, preferably 1 and particularly preferred 5, or when their octanol to aqueous buffer solution (pH 7) distribution ratio is 1, preferably 10, and particularly preferred greater than 50. Alternatively, or in addition to this, the drugs should reversibly and/or irreversibly bond to cell components at percentages greater than 10%, preferably greater than 50%, and particularly preferred greater than 80%. Preferred are substances that inhibit cell proliferation or inflammatory processes, or antioxidants such as Paclitaxel and other taxanes, Rapamycin and related substances, tacrolimus and related substances, corticoids, sexual hormones (estrogen, estradiol, antiandrogens) and related substances, statins, epothilones, probucol, prostacyclins, angiogenesis inducers, etc.

These substances are preferably present as a dry solid or as an oil on the surfaces of the various medical products. Preferred are the smallest particle sizes (mostly $<5$ microns, preferably $<1$ microns, particularly preferred $<0.1$ microns), particularly preferred are amorphous non-crystalline structures of the finest particle size that dissolve fast upon contact with tissue due to their large surface area and despite the generally poor water-solubility of the drugs and do not function as microcapsules, i. e. dissolve spontaneously and fast. It is sufficient that an effective dose is present in the form of smallest or amorphous particles; larger particles hardly contribute to the active agent concentration in the tissue but do not cause any interference. The dosage depends on the desired effect and the efficacy of the drug used It may be up to 5 $\mu g/mm^2$ and this value does not even constitute an upper limit. It is easier to handle smaller dosages.

Good adhesion to the surfaces of catheters, needles or wires on an improved absorption by the tissues is achieved by embedding strongly lipophilic active agents with poor water solubility in a readily water-soluble matrix substance. Suitable matrix substances are low-molecular (molecular weight $<5000$ D, preferably $<2000$ D) hydrophilic substances such as contrast agents and dyes used in vivo for various diagnostic procedures in medicine, sugar and related substances such as sugar alcohols, low-molecular polyethylene glycols, biocompatible organic and inorganic salts such as, for example, benzoates, salts and other derivatives of salicylic acid, etc. Examples of contrast agents are iodinated X-ray contrast agents and paramagnetic chelates, examples of dyes are indocyanine green, fluorescein, and methylene blue. Excipients may also improve shelf life of the products, cause specific additional pharmacological effects or be instrumental for quality control.

In another embodiment of the invention, the pharmaceutical active agents can be adsorbed to particles or applied to the surfaces of suitable medical products with a low-molecular matrix. Suitable particles once again are diagnostics known to be biocompatible such as ferrites and various contrast agents for sonography.

Excipients of any kind can be used at lower or higher doses than the active ingredients.

The medical products are coated using solutions, suspensions, or emulsions of the drugs and excipients mentioned above. Suitable media for solution, suspension or emulsion are, for example, ethanol, isopropanol, ethyl acetate, diethyl ether, acetone, dimethyl sulfoxide, dimethyl formamide, glycerin, water or mixtures thereof. Solvent selection is based on the solubility of the active agents and adjuvants, the wetting of the surfaces to be coated and the effect on the structure of the coating and particles remaining after evaporation of the solvent, their adhesion to the surface and active agent transfer to the tissue in very short contact times.

Coating can be carried out by immersing, spreading, applying with devices which deliver a defined volume to the surface or spraying at various temperatures and, optionally, vapor saturation of the solvents in the atmosphere. The procedure can be repeated several times using different solvents and excipients as may be required.

The balloons of folded balloon catheters ready for use can be given a surprisingly uniform, reproducible, dose-controllable coating without impairing catheter functionality by immersing them in solutions containing the active agent(s) or by other measures. When the balloons are repeatedly immersed in unsaturated active agent solutions, the active agent applied previously is not completely stripped off; instead, the active agent content of the balloons is increased in a reproducible manner.

Excess solution or excess substances from the coating solution that are loosely attached to the exterior can be removed with simple methods without impairing the efficacy of the coating.

The various types of medical devices designed and manufactured according to the invention come into short-term contact with the tissue, i. e. for a few seconds, minutes, or hours. It is desirable in some cases to pharmacologically treat the tissue with drugs in the immediate vicinity of the medical product, e. g. to prevent excess growth as a response to an injury or to reduce tumor growth, to enhance neovascularization or diminish inflammatory reactions. In all these cases, high local drug concentrations can be achieved for an astonishingly long time using the method described above. A major advantage is the extraordinary versatility of uses of the products and methods described.

A preferred application is to reduce hyperproliferation of vessel walls induced by dilatation with balloon catheters. This can be achieved when stents are implanted by coating these stents with drugs, but only for the vessel section covered by the stent. The coated balloon catheters also treat any areas at short distance in front of and just behind the stent that need treatment, they can treat the section where a stent has been implanted without requiring another stent implantation and vessels in which no stent is to be or can be implanted. An advantage as compared to the stents that release a drug over a long period of time is improved healing and simultaneous good inhibition of hyperproliferation and a reduced risk of thrombosis.

Several embodiments of the invention will be described below with reference to examples regarding the coating of balloon catheters, adhesion of the coating in the bloodstream, restenosis inhibition and active agent content of the catheters.

EXAMPLE 1

Coating an Expanded Balloon Catheter with Paclitaxel in Ethyl Acetate
Balloon catheters made by BMT, Oberpfaffenhofen/Munich, Germany, product name Joker Lite, balloon dimensions 2.5 mm by 20 mm, are inflated to the maximum and immersed full length for 1 minute in ethyl acetate, 18.8 mg Paclitaxel per ml, +1% pharmaceutical olive oil, dried: Paclitaxel content 39 micrograms (after extraction with ethanol, HPLC).

EXAMPLE 2

Coating a Folded Balloon Catheter with Paclitaxel in Ethyl Acetate
Balloon catheters made by BMT, Oberpfaffenhofen/Munich, Germany, product name Joker Lite, balloon dimensions 2.5 mm by 20 mm, are immersed full length in folded condition for 1 minute in ethyl acetate, 18.8 mg Paclitaxel per ml, +1% pharmaceutical olive oil, and dried:
Paclitaxel content 69 micrograms.

EXAMPLE 3

Coating a Folded Balloon Catheter with Paclitaxel in Ethyl Acetate
a) Balloon catheters made by BMT, Oberpfaffenhofen/Munich, Germany, product name Joker Lite, balloon dimensions 2.5 mm by 20 mm, are immersed full length in folded condition for 1 minute in ethyl acetate, 16.6 mg Paclitaxel per ml, and dried for 4 hours:
Paclitaxel content 54 micrograms.
b) Same procedure, but additional two times immersed for 5 seconds with 1 hour drying time after each immersion process in solution A (=3.33 ml ethyl acetate+100.0 mg of Paclitaxel) : Paclitaxel content 126 micrograms.
c) Same procedure, but additional four times immersed for 5 seconds with 1 hour drying time after each immersion process in the same solution:
Paclitaxel content 158 micrograms.

EXAMPLE 4

Coating a Balloon Catheter with Paclitaxel in Acetone
Dissolve 350 mg of Paclitaxel in 9.0 ml of acetone; balloon catheters made by BMT, Oberpfaffenhofen/Munich, Germany, product name Joker Lite, balloon dimensions 2.5 mm by 20 mm, are inflated to the maximum and immersed full length for 1 minute and removed. The solvent is dried for 12 hours at room temperature. Then the balloon is deflated and folded in the common way using a PTFE-coated tool. Optionally, one can crimp a stent of suitable dimensions onto the balloon: 29 micrograms of Paclitaxel on the balloon.

EXAMPLE 5

Coating a Balloon Catheter with Paclitaxel in Acetone
a) Immersion of folded balloon catheters made by BMT, product name Allegro, balloon dimensions 2.5 by 20 mm in a mixture of 0.15 ml ethanol+4.5 µl of Ultravist 300 (an X-ray contrast agent made by Schering AG, Berlin, Germany)+1.35 ml of acetone 0.8 mg Sudan red+30.0 mg of Paclitaxel:
The folded balloon sections of the catheters are immersed 5 times, the first time for one minute, then dried for 3 hours, then 4 times at 1 hour intervals for 5 seconds each; subsequently, a stent was crimped on and the catheter was sterilized in the common way using ethylene oxide: Paclitaxel content 172 micrograms, no decomposition products of the active agent were determined using HPLC
b) A saturated aqueous mannitol solution is used instead of Ultravist 300
c) A saturated aqueous sodium salicylate solution (pH 7.5) is used instead of Ultravist 300
d) 5 mg of acetylsalicylic acid are added to the completed solution according to (5a).
e) 5 mg of glycerin are added to the completed solution according to (5a).

EXAMPLE 6

Adhesion of the Active Agent in the Bloodstream
12 balloon catheters made by BMT, product name Allegro, balloon dimensions 2.5 by 20 mm, were used. The folded balloon sections of 6 catheters each were either 5 times immersed in [0.15 ml of ethanol+4.5 µl of Ultravist 300+1.35 ml of acetone+0.8 mg of Sudan red+30.0 mg Paclitaxel] or 5 times in [1.5 ml of ethyl acetate+0.8 mg Sudan red+31.0 mg Paclitaxel], the first time for 1 minute each with 3 hours of drying time, then 4 times for 5 seconds each at 1 hour intervals; then 3 of the folded balloons of each group were gently moved for 5 minutes at 37° C. in 50 ml of human blood and removed to determine the Paclitaxel content: Reduction of mean values (n=3 per coating method) by 5 minutes of movement in blood as compared to 3 control catheters that were not incubated in blood.

Acetone: 12%
Ethyl acetate: 10%

EXAMPLE 7

Examination of restenosis inhibition after angioplasty and stent implantation in coronary arteries of pigs.

Folded balloon catheters of the Joker Lite type made by BMT, 3.5 by 20 mm or 3.0 by 20 mm were immersed for 1 minute either in
   solution A) 3.33 ml of ethyl acetate (EA)+100.0 mg of Paclitaxel, or in
   solution B) 0.45 ml of ethanol+100 µl of Ultravist−370+ 4.5 ml acetone (ac)+150.0 mg Paclitaxel
and dried over night at room temperature. One more (low dose=L) or 4 more (high dose=H) immersion process(es), respectively, were carried out for just five seconds at 1 hour intervals on the next day.

Active agent content after 2 immersions in solution (B) averaged 250 µg, after 5 immersions in solution (B) 500 µg, in solution (A) 400 µg.

The catheters coated with Paclitaxel or uncoated were used to implant stents into the left anterior or lateral coronary artery of a total of 22 pigs, and the vessels were slightly overdilated to stimulate restenosis by tissue hyperplasia. The animals were reangiographed after 5 weeks, and the vessel stenosis shown in the angiograms was measured using an automatic computer program.

| Group | Stenosis (%) |
|---|---|
| Uncoated | 50.49 |
| AcL | 20.22 |
| EAH | 36.01 |
| AcH | 0.86 |
| P | .004 |

Quantitative coronary angiography 5 weeks after stent implantation with uncoated and coated catheters; stenosis=reduction of lumen diameter in percent in the area of the stent as compared to the lumen diameter immediately after stent implantation; mean value and statistical significance of the effect of treatment.

EXAMPLE 8

Active Agent Content of the Catheters after Vessel Dilatation and Stent Implantation After stent implantation and removal from the animals, the balloons from Example 8 ca. 3 cm in length were cut off the balloon catheters and placed in 1.5 ml of ethanol. Paclitaxel content was determined using HPLC. All available coated balloons and a selection of uncoated balloons were examined.

Coronary,

| | | | |
|---|---|---|---|
| 3.0 by 20 mm, coating: | Ac high | 38 ± 4 µg | (n = 4) |
| | Ac low | 22 ± 5 µg | (n = 2) |
| | EEE high | 41 | (n = 1) |
| 3.5 by 20 mm, coating: | Ac high | 37 ± 10 µg | (n = 8) |
| | Ac low | 26 ± 6 µg | (n = 8) |
| | EEE high | 53 ± 9 µg | (n = 9) |
| Uncoated (independent of size and vessel area) | | 0.9 ± 1.0 µg | (n = 7) |

It follows from Example 6 that a maximum of 10% of the dose is lost before the balloon is inflated and about 10% of the dose remain on the balloon.

EXAMPLE 9

Probucol is added to acetone at a concentration of 100 mg per ml; the solution is used to coat balloon catheters as described in the above examples.

EXAMPLE 10

Rapamycin is dissolved at a concentration of 10 mg/ml in diethyl ether. The balloon sections of the catheters are coated as described in the above examples; after removal from the coating solution, the balloons should be brought into a horizontal position and continuously be turned around their longitudinal axis as soon as possible.

EXAMPLE 11

Epothilone B is dissolved in ethyl acetate at a concentration of 2 mg/ml; the solution is used to coat balloon catheters as described in the above examples.

The invention claimed is:
1. A method of treating a vascular disease or circulation disturbance comprising: administering a device to affected tissue of a patient, wherein said device is a balloon catheter medical device comprising:
   a balloon surface having paclitaxel embedded in a low-molecular weight matrix substance adhered thereto and dried,
   wherein the dried paclitaxel is immediately releasable after coming into contact with tissue.
2. The method according to claim 1, wherein said low-molecular weight matrix substance has a molecular weight of less than 5000 D and is selected from contrast agents and dyes used in vivo, sugars, sugar alcohols, low-molecular polyethylene glycols, and biocompatible organic and inorganic salts.
3. The method according to claim 1, wherein said low-molecular weight matrix substance is selected from iodinated X-ray contrast agents, paramagnetic chelates, indocyanine green, fluorescein, and methylene blue.
4. The method according to claim 1, wherein said low-molecular weight matrix substance is a readily water-soluble hydrophilic matrix substance.
5. The method according to claim 1, wherein the low-molecular weight matrix substance has a molecular weight of less than 5000 D.
6. The method according to claim 1, wherein the low-molecular weight matrix substance has a molecular weight of less than 2000 D.
7. The method according to claim 1, wherein said balloon catheter medical device further comprises a stent.

8. The method according to claim 1, wherein the balloon catheter medical device does not comprise a stent.

9. The method according to claim 1, wherein the balloon surface has preformed longitudinal folds maintaining an inclination to refold after inflation.

10. The method according to claim 9, wherein at least an area covered by the folds is covered with the paclitaxel.

11. The method according to claim 9, wherein only an area covered by the folds is covered with the paclitaxel.

12. The method according to claim 1, wherein the balloon surface consists of a very smooth material to which the paclitaxel embedded in the low-molecular weight matrix substance adheres sufficiently well to resist forces required for folding, essentially without damage.

13. The method according to claim 1, wherein the balloon surface is coated by immersion in a low-viscosity paclitaxel solution while in a fully folded condition.

14. The method according to claim 1, wherein the paclitaxel is present as a dry solid on the balloon surface.

15. The method according to claim 14, wherein an effective dose of the paclitaxel includes amorphous structures with particle sizes ranging from <0.1 micron to 5 microns that dissolve quickly due to their large surface area and despite the poor water-solubility of the paclitaxel.

16. The method according to claim 1, wherein the low-molecular weight matrix substance is hydrophilic.

17. The method according to claim 1, wherein the paclitaxel is applied to the balloon surface with said low-molecular weight matrix substance.

18. The method according to claim 1, wherein the balloon surface further comprises a substance that influences the gliding quality of the device or that prevents blood coagulation.

19. A method of opening a passage in the body comprising:
   administering a device to said body, wherein said device is a balloon catheter medical device comprising:
   a balloon surface having paclitaxel embedded in a low-molecular weight matrix substance adhered thereto and dried,
   wherein the dried paclitaxel is immediately releasable after coming into contact with tissue.

20. A method for tumor treatment comprising:
   administering a device to a patient, wherein said device is a balloon catheter medical device comprising:
   a balloon surface having paclitaxel embedded in a low-molecular weight matrix substance adhered thereto and dried,
   wherein the dried paclitaxel is immediately releasable after coming into contact with tissue.

* * * * *